(12) United States Patent
Getsay

(10) Patent No.: US 8,939,951 B1
(45) Date of Patent: Jan. 27, 2015

(54) FLUID COLLECTION DEVICE

(71) Applicant: James G. Getsay, Harmony, PA (US)

(72) Inventor: James G. Getsay, Harmony, PA (US)

( * ) Notice: Subject to any disclaimer, the term of this patent is extended or adjusted under 35 U.S.C. 154(b) by 92 days.

(21) Appl. No.: 13/815,853

(22) Filed: Mar. 15, 2013

(51) Int. Cl.
  *A61M 1/00* (2006.01)
  *A61M 27/00* (2006.01)
  *A61F 13/00* (2006.01)

(52) U.S. Cl.
  CPC ............. *A61M 1/008* (2013.01); *A61M 1/0023* (2013.01); *A61M 27/00* (2013.01); *A61M 1/0058* (2013.01); *A61F 2013/0054* (2013.01); *A61M 1/0086* (2014.01); *A61F 2013/00536* (2013.01); *A61F 13/00068* (2013.01); *A61M 1/0084* (2013.01)
  USPC ........... 604/319; 604/540; 604/327; 604/541; 604/543

(58) Field of Classification Search
  CPC . A61M 1/0023; A61M 1/0058; A61M 1/008; A61M 1/0084; A61M 1/0086; A61M 25/00; A61M 25/0009; A61M 27/00; A61M 39/00; A61M 2025/00; A61M 2025/0067; A61M 2025/0068; A61M 2027/00; A61M 1/0088; A61M 1/0092; A61M 1/0056; A61F 13/00068; A61F 2013/00536; A61F 2013/0054
  USPC .................... 604/8, 9, 10, 540, 541, 543, 544
  See application file for complete search history.

(56) References Cited

U.S. PATENT DOCUMENTS

| | | | | |
|---|---|---|---|---|
| 3,753,439 A | * | 8/1973 | Brugarolas et al. ............. | 604/43 |
| 5,014,389 A | * | 5/1991 | Ogilvie et al. ................... | 15/353 |
| 5,100,395 A | * | 3/1992 | Rosenberg ..................... | 604/284 |
| 5,720,078 A | * | 2/1998 | Heintz .......................... | 15/415.1 |
| 5,762,640 A | * | 6/1998 | Kajiwara et al. ............... | 604/313 |
| 6,099,513 A | * | 8/2000 | Spehalski ...................... | 604/264 |
| 7,223,263 B1 | * | 5/2007 | Seno ............................. | 604/541 |
| 7,753,902 B1 | * | 7/2010 | Mansour et al. ............... | 604/541 |
| 7,790,945 B1 | * | 9/2010 | Watson, Jr. .................... | 602/43 |
| 8,419,696 B2 | * | 4/2013 | Wilkes .......................... | 604/313 |
| 2002/0161346 A1 | * | 10/2002 | Lockwood et al. ............. | 604/315 |
| 2003/0032919 A1 | * | 2/2003 | Hartig et al. ................... | 604/47 |
| 2004/0006331 A1 | * | 1/2004 | Shchervinsky ................ | 604/541 |
| 2004/0193095 A1 | * | 9/2004 | Shadduck ......................... | 604/8 |
| 2006/0041247 A1 | * | 2/2006 | Petrosenko et al. ............ | 604/543 |
| 2006/0258996 A1 | * | 11/2006 | Opie et al. ..................... | 604/317 |
| 2007/0219512 A1 | * | 9/2007 | Heaton et al. ................. | 604/304 |
| 2009/0163893 A1 | * | 6/2009 | Opie et al. ..................... | 604/541 |
| 2009/0264838 A1 | * | 10/2009 | Livne et al. .................... | 604/290 |
| 2010/0179516 A1 | * | 7/2010 | Bengtson et al. .............. | 604/543 |
| 2010/0228206 A1 | * | 9/2010 | Larsson ......................... | 604/319 |

(Continued)

*Primary Examiner* — Adam Marcetich
(74) *Attorney, Agent, or Firm* — Eckert Seamans Cherin & Mellott, LLC; Philip E. Levy

(57) ABSTRACT

A fluid collection device for withdrawing a fluid from an object includes a chamber having a plurality of apertures and an opening for flow of the fluid. A tube is positioned in fluid communication with the opening of the chamber for withdrawing fluid out of the chamber. At least one of the apertures is positioned within a recess for substantially preventing clogging of the apertures during collection and removal of the fluid. The plurality of apertures may be interconnected by grooves for directing the flow and preventing clogging of the apertures. The tube has a plurality of holes that are positioned within the chamber and held in place with a retaining ring. The apertures may be positioned so that spaces are provided between the apertures for placement of the tube or other devices. Exposed edges of the chamber and recesses are radiused for reducing irritation to a person.

4 Claims, 5 Drawing Sheets

(56) References Cited

U.S. PATENT DOCUMENTS

| | | |
|---|---|---|
| 2010/0249691 A1* | 9/2010 | Van Der Mooren et al. ..... 604/9 |
| 2010/0280469 A1* | 11/2010 | Hall et al. ..................... 604/319 |
| 2011/0202059 A1* | 8/2011 | Webb et al. ..................... 606/59 |
| 2012/0016324 A1* | 1/2012 | Long et al. ..................... 604/319 |
| 2013/0165821 A1* | 6/2013 | Freedman et al. ................ 601/2 |
| 2013/0253409 A1* | 9/2013 | Burnett ............................. 604/9 |
| 2013/0274717 A1* | 10/2013 | Dunn ............................. 604/541 |

* cited by examiner

FLUID COLLECTION DEVICE

BACKGROUND OF THE INVENTION

The invention relates to devices that transfer fluids and, more particularly, to devices for the collection and removal of fluid from an object.

During medical treatment of a person, may different types of fluids may be introduced into a person's body, and removed from a person's body. As an example, during treatment for cancer, chemotherapy drugs may be disbursed into a person's peritoneal cavity, mixed with other bodily fluids, and the combination of fluids subsequently removed from the person's body. Other examples of fluids may include saline solution, blood, drugs, or any other desired fluid that may be necessary for treatment of an individual.

Various types of equipment are used for withdrawing fluid and other particulates from a person's body during a medical procedure, such as surgery. For example, various types of surgical aspirators, tubing and fittings are used during the treatment of a person.

Often during the use of the aspirator or other medical removal device, the holes of the device become clogged or plugged with pieces of debris, such as tissue, blood clots, or the like. Currently, several types of tip guards, sleeves, or other devices have been used in combination with the aspirator in an attempt to prevent clogging of the holes during fluid removal.

Therefore, what is needed is an apparatus and method for withdrawing a fluid from an object that does not clog during use and that can easily and efficiently collect and remove the fluid.

SUMMARY OF THE INVENTION

A fluid collection device for transferring a fluid includes a chamber having a plurality of apertures positioned through at least one side of the chamber for the flow of the fluid into the chamber. At least one of the plurality of apertures is positioned within a recess for substantially preventing clogging of the plurality of apertures during collection of the fluid. The diameter of the plurality of apertures is smaller than the diameter of the recess for substantially preventing clogging of the apertures.

The chamber has an opening for withdrawing the fluid from the chamber and a tube is positionable at the opening of the chamber for providing fluid communication between the chamber and the tube for withdrawing the fluid from the chamber through the tube. The tube includes a bore and at least one hole, having the bore and the at least one hole positioned within the chamber for providing additional access points for the flow of the fluid therethrough and out of the chamber. The tube is rotatable and has an angled portion for directing the flow of fluid. A retaining ring is positionable about the tube and positionable within the chamber adjacent to the opening for retaining the tube within the chamber.

The first side of the chamber has at least one first space positioned between the plurality of apertures for placement of other devices. The first side of the chamber also has a second space positioned between the plurality of apertures, and the second side of the chamber has a third space positioned between the plurality of apertures for placement of the tube.

The first and second sides of the chamber further include at least one groove positioned connecting at least a portion of the plurality of apertures for providing a pathway for the flow of the fluid and for substantially preventing clogging of the plurality of apertures. The first and second sides may also include at least one groove positioned extending from at least a portion of the plurality of apertures outwardly for providing a pathway for the flow of the fluid and for substantially preventing clogging of the plurality of apertures.

The fluid collection device may further include a retaining member for attachment of other devices thereto, making the fluid collection device usable in combination with other devices. A stabilizer having a surface and a bore may be used for providing stabilization during collection of the fluid. The chamber is formed from a flexible material making the device less invasive during use in a person's body.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings, wherein:

DESCRIPTION OF THE PREFERRED EMBODIMENT

The invention described herein provides an apparatus and method for withdrawing fluid from an object. The apparatus and method can be used in a medical environment, such as during surgery, treatment, or any other procedure, or can be used in any other type of environment or application. The fluid to be removed may be fluids used during medical procedures, such as chemotherapy drugs, saline solution, or other fluids used during treatment. The fluid can also include blood or other bodily fluids, small blood clots, small pieces of tissue, such as fat, muscle, or the like, or any other smaller types of material. The apparatus is sized for preventing larger pieces of material from passing through.

The object may include a specific area or regions of a person's body, such as for chemotherapy treatment of cavities, for example, the peritoneal space outside of the stomach or the pleural space outside of the lungs of a person, or for any other desired treatment areas. For areas other than a person's body, the object may include any desired area that needs fluid collection or removal.

Figure 1:
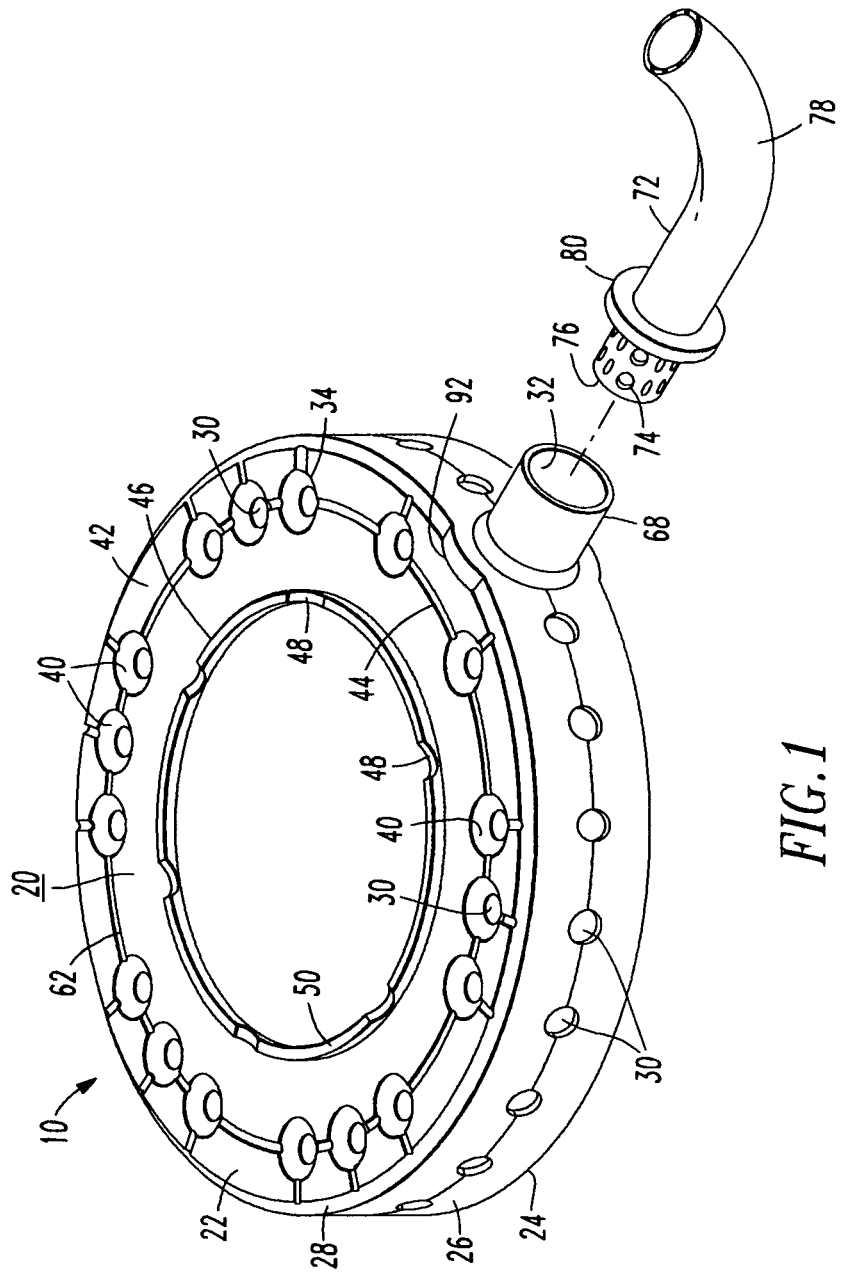
FIG. 1 is an isometric view of a fluid collection device.

Referring to FIGS. 1-6, a fluid collection device 10 includes a chamber 20 having at least one wall, such as a first side 22, a second side 24, and a third side 26. The first side 22, second side 24 and third side 26 are the walls that form the housing of the collection chamber 20. The first, second and third sides 22, 24 and 26 enclose a hollow space 18 formed within the chamber 20. The fluid may flow into the hollow space within the chamber 20. The first, second and third sides 22, 24 and 26 may be separately formed pieces, may be integrally formed together as a single piece, or any suitable configuration. As one example, as shown in FIG. 1, the chamber 20 may be formed from two pieces that snap together, such as the first side 22 and a portion of the third side 26 being integrally formed together forming a first component. The second side 24 and a portion of the third side 26 are integrally formed together forming a second component that is engagable with the first component for forming the chamber 20.

Preferably, the chamber 20 has radiused edges, such as edge 28, for providing comfort to the patient and minimizing irritation and trauma to the person. The first, second, and third sides 22, 24, 26 have a plurality of apertures 30 for transferring fluid therethrough. The chamber 20 also has an opening 32 for transferring fluid. Preferably, fluid flows into the chamber 20 through the plurality of apertures 30 and the fluid flows out of the chamber 20 through the opening 32. The diameter of the opening 32 is sized for handling a larger volume of fluid as compared to the diameter of the plurality of apertures 30.

The plurality of apertures 30 in the first side 22 and the second side 24 are each positioned within a recess 40. Preferably, the diameter of the apertures 30 is smaller than the diameter of the recess 40 for forming a divot within the first side 22 and the second side 24. The recess 40 or divot is an elongated protuberance or protrusion extending into the interior of the chamber 20. The recess 40 has a first surface, or first edge 34, and a second surface, or second edge 36, that may be curved, arched, flat, straight, concave, convex, or any suitable shape. The aperture 30 is positioned at the bottom or second edge 36 of the recess 40. The first edge 34 is positioned at the opening of the recess 40. The opening or first edge 34 has a larger diameter as compared to the diameter of the second edge 36 or aperture 30.

Preferably, all edges of the first surfaces 34 and the second surfaces 36 of the recess 40 are radiused, having no sharp edges for minimizing damage to the patient and reducing irritation and trauma to the person. Additionally, the radiused edges of the surfaces 34 and 36 more uniformly funnel the fluid into the recesses 40 and out of the apertures 30. The shape of the recess 40 or divot substantially prevents clogging of the apertures 30 from particles or other debris that may be pulled by a suction or the like during collection and withdrawal of the fluid.

The apertures 30 of the third side 26 may or may not be positioned within the recess 40. The plurality of apertures 30 provide a multitude of access holes for the introduction of the fluid therethrough. In the event that a few of the apertures 30 become clogged, the use of a plurality of apertures 30 in the chamber 20 provides alternative entrance areas into the chamber 20.

Figure 2:
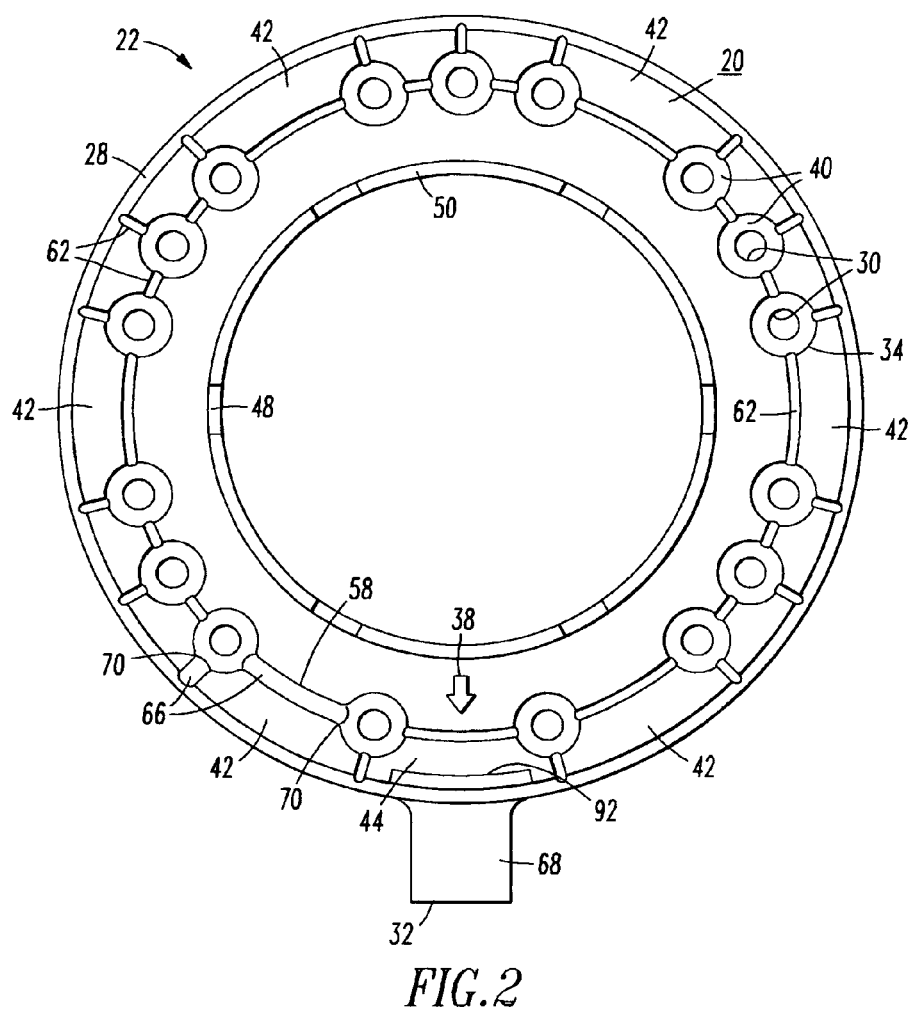
FIG. 2 is a plan view of a first side of the fluid collection device showing alternative embodiments of a groove.

As one example, referring to FIG. 2, the chamber 20 is disc shaped and may be formed from a flexible material, a rigid material, or any other suitable material. The first side 22 of the chamber 20 includes the plurality of apertures 30 positioned circumferentially. The apertures 30 are positioned in spaced apart relationship to one another, and may be positioned in clusters, evenly spaced with respect to one another, or in any various position. The first side 22 has at least one first space 42 and a second space 44 positioned between the apertures 30.

An orientation marking, such as an arrow 38 may be positioned on at least one of the first, second, and third sides 22, 24 and 26 of the chamber 20. Preferably, as shown in FIG. 2, the arrow 38 is located on the second side 24 so that the arrow 38 can be viewed while the fluid collection device 10 is in use. The arrow 38 can be aligned with a person's incision, a piece of medical equipment, or the like for providing a specific orientation of the fluid collection device 10.

The first side 22 of the chamber 20 additionally may have a retaining member 50. The retaining member 50 is a lip, raised edge, or the like for engagement with another object. The retaining member 50 may be circular or have any shape corresponding to the shape of the device desired to be attached thereto. Preferably, the retaining member 50 has at least one indentation 48. As one example, referring to FIGS. 4-6, positioned on the raised edge 50, the fluid collection device 10 may be attached to an object, such as a fluid distribution device 52. The fluid distribution device 52 has a disc shape and is seated in the circular raised edge 50 of the retaining member 50. The retaining member 50 is sized so that the fluid distribution device 52 snaps into and is snugly held by the retaining member 50. The fluid distribution device 52 has a disbursement housing 54 attached to a plurality of tubing 56 for the distribution of fluid. The tubing 56 is positionable to extend along or within the spaces 42 of the first side 22 and between the clusters of apertures 30 so that the tubing 56 does not block or restrict fluid flow through the apertures 30. The tubing 56 may be seated within the indentations 48 of the retaining member 50. The indentations 48 provide a positive orientation for the tubing 56. The engagement together of the fluid collection device 10 and the fluid distribution device 52 allows the combination of the two devices 10 and 52 to distribute fluid into and collect fluid from the object in a compact unit.

Additionally, preferably the retaining member 50 has at least one radiused edge, such as edge 46, for reducing irritation and trauma to the person. The retaining member 50 may have all edges radiused. Also, the indentations 48 may be radiused.

Preferably, the fluid distribution device 52 and the fluid collection device 10 are removably attached together, such as by snapping the pieces together, enabling either one or the other, or both devices to be used at a time. Alternatively, the fluid distribution device 52 and the fluid collection device 10 can be adhesively attached together, mechanically attached together, or the like.

Figure 3:
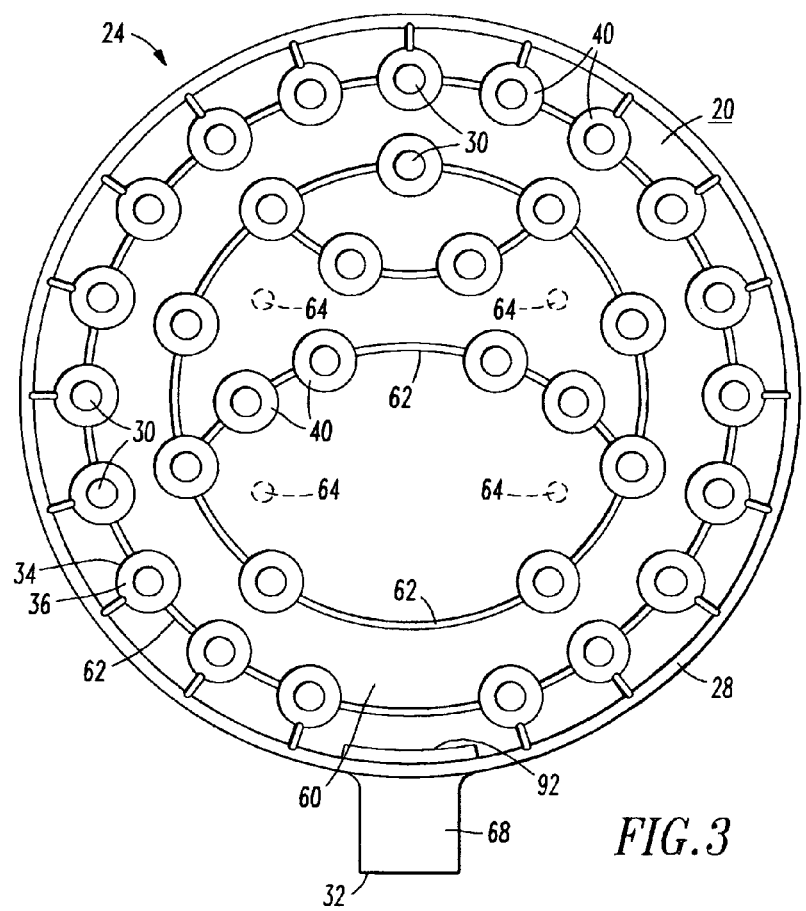
FIG. 3 is a plan view of a second side of the fluid collection device.
Figure 3A:
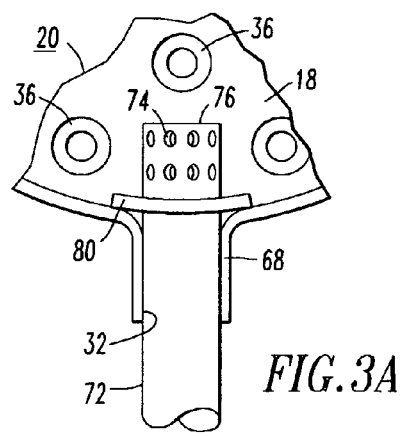
FIG. 3A is a partial view of a tube having a plurality of holes extending into a chamber of the fluid collection device, and showing a retaining ring.

As an example, referring to FIG. 3, the second side 24 of the chamber 20 also has the plurality of the apertures 30 positioned circumferentially and in various positions. The apertures 30 are positioned in spaced apart relationship to one another, and may be positioned in various patterns or evenly spaced with respect to one another. The second side 24 has a third space 60 positioned between the apertures 30.

Both of the first and second sides 22 and 24 may have at least one groove 62 interconnecting the recesses 40. If a recess is not used as with the third side 26, then at least one groove 62 may interconnect with the apertures 30. The groove 62 is a trough, recess, or the like for directing the flow of fluid. The groove 62 also acts to substantially prevent clogging or seating of material that may prevent fluid flow through the apertures 30. The grooves 62 may extend radially or outwardly from the apertures 30 for directing the flow of the fluid. The grooves 62 may also extend in an arc for providing a curved or circular pathway for connecting the recesses 40 and apertures 30 together for directing the fluid flow. The grooves 62 provide a pathway for the flow of the fluid. The grooves 62 fluidly interconnect the plurality of apertures 30. Preferably, the grooves 62 connect to each of the apertures 30, but alternatively, may connect only a portion of the plurality of apertures 30 together.

Figures 4, 5:
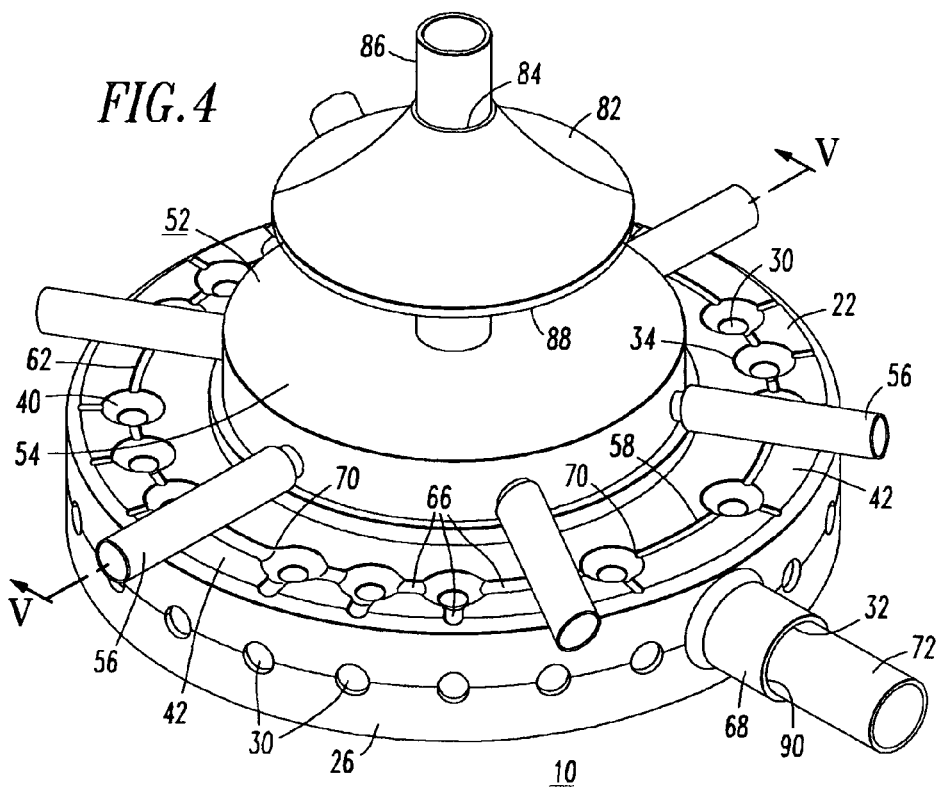
FIG. 4 is an isometric view of the fluid collection device attached to a fluid distribution device.
FIG. 5 is a cross-sectional view of the fluid collection device attached to the fluid distribution device.
Figure 6:
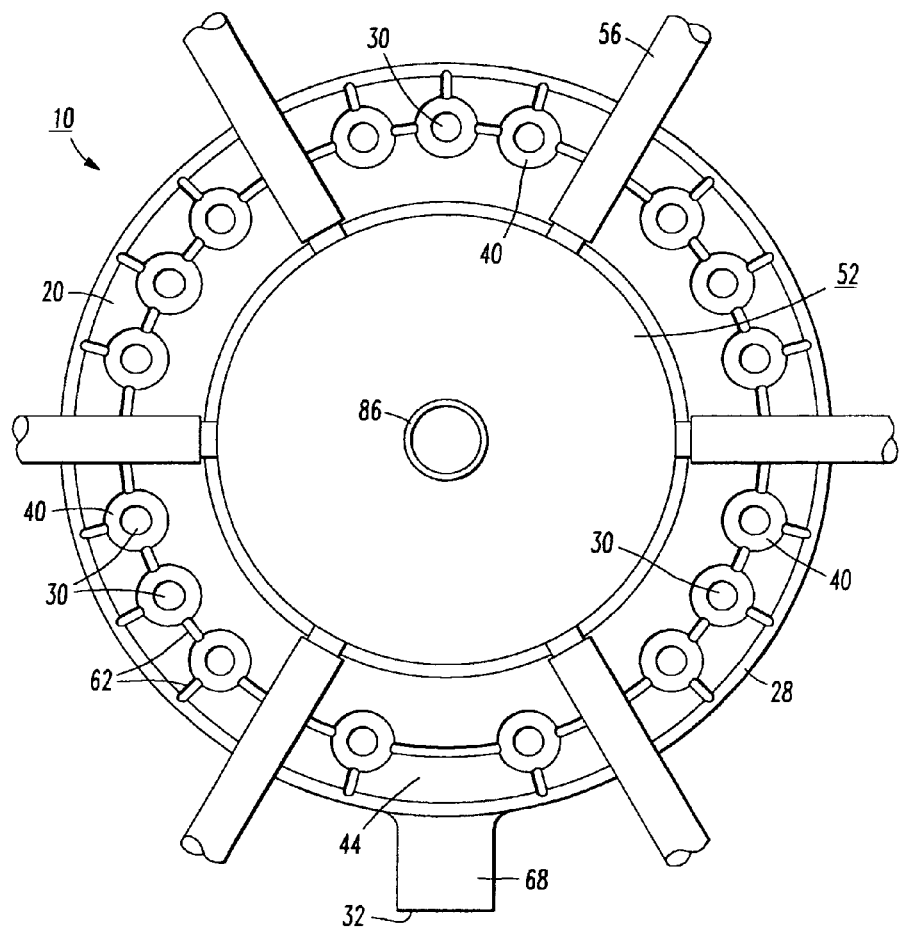
FIG. 6 is a plan view of the fluid collection device attached to the fluid distribution device.

Preferably, the groove 62 has radiused edges, such as a radiused shoulder 58 and radiused corners 70, for providing comfort to the person and facilitating flow of the fluid. The grooves 62 may be shallow, deep or any suitable depth and width for substantially preventing clogging of the fluid collection device 10 and facilitating flow of the fluid. Referring to FIGS. 2 and 4, a portion 66 of the groove 62 is shown having a greater depth and width than adjacent portions of the groove 62. The groove 62 may have a uniform size throughout the chamber 20, or may have varying sizes for facilitating flow of the fluid and substantially preventing clogging.

The chamber 20 may have at least one support 64 to prevent the first and second sides 22 and 24 from collapsing toward one another. The support 64 is a boss, circular protuberance, elongated support, or the like for structurally supporting the first and second sides 22 and 24. The support 64 may be one piece attached to either one of the first and second sides 22 and 24 and contacting the other of the first and second sides 22 and 24 during use, may be two pieces having one piece attached to each of the first and second sides 22 and 24 and engagable with one another, or any other suitable construction.

The chamber 20 may or may not have an extension 68 extending from the third side 26 of the chamber 20. Alternatively, the extension 68 may be positioned in any desired location. The opening 32 is positioned at the extension 68, or alternatively, flush with an outside wall of the chamber 20.

A tube 72 is used for withdrawing the fluid from the chamber 20. The tube 72 is sized for engagement with the opening 32 of the chamber 20. Preferably, the tube 72 is disposed through the opening 32, through the extension 68, and is positioned partially within the interior of the chamber 20. Alternatively, the tube 72 may be attached to the third side 26 of the chamber for providing the fluid communication between the tube 72 and the chamber 20. The tube 72 has at least one hole 74 in a wall of the tube 72 for flow of the fluid therethrough. Preferably, a plurality of the holes 74 are positioned at one end of the tube 72. The at least one hole 74 is positioned within the chamber 20 for providing additional access points for the fluid to flow through. In the event that the bore 76 of the tube 72 becomes clogged, the fluid may flow through the at least one hole 74.

The tube 72 is preferably positioned along the space 44 of the first side 22 and along the space 60 of the second side 24 for reducing or eliminating blockage of the plurality of apertures 30 of the chamber 20. Also, this positioning avoids contact or interference of the tube 72 with the divots 40 that protrude into the interior of the chamber 20.

The tube 72 is rotatable within the opening 32 for enabling a person to adjust the positioning of the tube 72 with respect to the chamber 20 and with respect to the object that the fluid collection device 10 is positioned in. Additionally, there may be a channel 90 formed between the outside diameter of the tube 72 and the inside diameter of the opening 32 for allowing seepage of the fluid therethrough for providing an additional access point for the flow of the fluid. The tube 72 may also be straight, have an elbow or angled portion 78, be at least partially bent, or any other suitable shape for providing a variety of positions of the tube 72 during use. The tube 72 is preferably flexible, but alternatively, may be rigid or any suitable material.

Referring to FIG. 1, a retaining ring 80 is sized for positioning about the tube 72 and is positionable within the chamber 20. The inside diameter of the retaining ring 80 is substantially equal to or slightly smaller than the outside diameter of the tube 72 for enabling the retaining ring 80 to be snugly disposed on the tube 72. The outside diameter of the retaining ring 80 is larger than the diameter of the opening 32 of the chamber 20 for preventing the retaining ring 80 from slipping through the opening 32, thereby holding the tube 72 securely in position with respect to the chamber 20. The retaining ring 80 may have a square profile, a round profile, or any other suitable shape. The retaining ring 80 may be adhesively attached to the tube 72, frictionally secured, mechanically attached, or the like for securing the ring 80 to the tube 72 and for preventing the tube 72 from coming out of the chamber 20.

The chamber 20 may have a retaining groove 92 positioned in the first side 22 and the second side 24 for seating the retaining ring 80 within the groove 92 within the chamber 20. The retaining groove 92 is a protruding arch extending outwardly from the chamber and is sized for housing the ring 80 therein. Preferably, the retaining ring 80 is rotatable within the groove 92 for manipulation of the tubing 72 with respect to the chamber 20.

A stabilizer 82 may be used to assist in stabilizing the fluid collection device 10 during use. The stabilizer 82 has a bore 84 therethrough that has a diameter sized for the disposition of a tube 86 through the bore 84. The tube 86 introduces fluid into the fluid distribution device 52. The stabilizer 82 is slidable along the length of the tube 86 for adjusting the position of the stabilizer 82 along the length of the tube 86. The bore 84 is sized so that when the stabilizer 82 is positioned in the desired location along the tube 86, the stabilizer 82 is snugly held in that position. The stabilizer 82 has a surface 88 which contacts the object for supporting the fluid collection device 10 during use. The stabilizer 82 acts as a clamp for securing or holding the components stationary with respect to the person or object.

Preferably, the components of the fluid collection device 10 are constructed from a clear material for enabling a person to visually observe the fluid being collected and withdrawn from the object.

In operation, as an example, the fluid collection device 10 is positioned in an object, such as a person's body during surgery. If the fluid collection device 10 is used in combination with the fluid distribution device 52, then the fluid collection device 10 is positioned below the fluid distribution device 52, allowing fluid to flow into the body from a higher point, sink due to gravity, and to be removed from the body at a lower point in the body. The fluid distribution device 52 is secured within the retaining member 50. Otherwise, the fluid collection device 10 alone may be positioned in any desired location in an object.

The tube 72 is rotated or positioned to extend from the chamber 20 to outside of the person's body in a desired position. If the fluid distribution device 52 is used, after the person's body is closed with the fluid collection device 10 within the body, the stabilizer 82 is slid along the tube 86 until the stabilizer 82 contacts the person's body and acts like a clamp against the person's body.

A withdrawal force, such as suction, siphon, gravity or the like, is applied to the tube 72 enabling fluid to be pulled from within the body, through the plurality of apertures 30 of the chamber 20, through the holes 74 and the bore 76 of the tube 72, through the opening 32, and out of the body or other object through the tube 72.

An advantage of the fluid collection device 10 is that the design of the plurality of apertures 30 provides a greater opportunity for fluid to flow into the chamber 20 due to a multitude of access points for the fluid to flow through. The use of a plurality of holes 74 in the tube 72 and the channel 90 also provide multiple access points.

Another advantage is that the design of the recesses 40 and grooves 62 substantially prevent or reduce clogging of the plurality of apertures 30 to facilitate continuous fluid flow into the chamber 20 during use.

Another advantage is the use of the retaining member 50, the spaces 42, and the indentation 48 for engagement with other devices, such as other pieces of medical equipment, for example the fluid distribution device 52, or the like. The use of spaces 44 and 60 is advantageous for placement of other devices, such as tubing, medical equipment, or any desired device, without interference with the divots 40 or plurality of apertures 30.

Yet another advantage is the use of a flexible material for the chamber 20. The soft or semi-flexible chamber 20 is adaptable to the various crevices within a person's body or other object for fitting the chamber 20 in a desired position. The flexible material is less invasive during use in a person's body. The flexible material makes the chamber 20 usable in a variety of other situations. The flexible tube 72 also allows for various positioning of the chamber 20 and tube 72.

Another advantage is the use of radiused edges on all exposed surfaces. This eliminates all rough or sharp edges that may cause discomfort to a person during use of the fluid collection device. The use of radiused edges reducing irritation and trauma to the patient.

An advantage of the retaining member is that the fluid collection device is usable in combination with other devices, such as medical devices or any other suitable application. The fluid collection device can be used alone, or in combination with other devices.

Thus there has been shown and described a novel fluid collection device and method which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

I claim:

1. A fluid collection device for transferring a fluid, comprising:
    a chamber having a first side and a second side positioned in space apart relationship to one another, and having a third side positioned between the first and the second sides, the first, second and third sides forming the chamber therebetween;
    the chamber having a plurality of apertures positioned through the first, second and third sides for flow of the fluid into the chamber;
    the chamber having at least one recess, and at least one of the first and second sides of the chamber having each of the plurality of apertures positioned within one of the at least one recess for substantially preventing clogging of the plurality of apertures during collection of the fluid, the diameter of the plurality of apertures being smaller than the diameter of the at least one recess for substantially preventing clogging of the plurality of apertures;
    the chamber having at least one groove positioned connecting at least a portion of the at least one recess for providing a pathway for flow of the fluid through the at least one groove, through the at least one recess and into the plurality of apertures;
    the chamber having an opening positioned in one of the at least one first, second and third sides for withdrawing the fluid from the chamber;
    a tube positioned in fluid communication with the opening of the chamber for withdrawing the fluid from the chamber through the tube
    the chamber having a retaining member extending therefrom, and the retaining member having a plurality of indentations spaced around the retaining member;
    a fluid distribution device having a disbursement housing attached to a plurality of tubing member extending therefrom for the distribution of the fluid, the fluid distribution device engageable with the retaining member of the chamber of the fluid collection device, wherein each of the tubing members is seated in a respective one of the indentations of the retaining member; and
    the chamber having a plurality of first spaces, each of the first spaces being positioned between a respective pair of the apertures for placement of the plurality of the tubing members of the fluid distribution device for reducing restriction of the fluid flow through the plurality of apertures and from the chamber.

2. The fluid collection device according to claim 1, further comprising;
    the first and second sides of the chamber having the at least one groove positioned connecting at least a portion of the at least one recess for providing a circular pathway for flow of the fluid through the at least one groove and through the at least one recess for interconnecting the plurality of apertures for enhancing flow of the fluid and for substantially preventing clogging of the plurality of apertures; and
    the first and second sides of the chamber having the at least one groove positioned extending from at least a portion of at least one recess outwardly for providing a radial pathway for flow of the fluid for interconnecting the plurality of apertures for enhancing flow of the fluid and for substantially preventing clogging of the plurality of apertures.

3. The fluid collection device according to claim 1, wherein the at least one recess is an elongated protuberance having a first edge and a second edge, the first and the second edges having radiused edges for facilitating flow of the fluid and for substantially preventing clogging of the plurality of apertures.

4. The fluid collection device according to claim 1, wherein the first spaces are spaced around the first surface of the chamber, wherein the plurality of indentations are symmetrically spaced around the retaining member with each indentation being aligned with a respective one of the first spaces.

* * * * *

UNITED STATES PATENT AND TRADEMARK OFFICE
CERTIFICATE OF CORRECTION

PATENT NO. : 8,939,951 B1
APPLICATION NO. : 13/815853
DATED : January 27, 2015
INVENTOR(S) : James G. Getsay Page 1 of 1

It is certified that error appears in the above-identified patent and that said Letters Patent is hereby corrected as shown below:

In the Specification
Column 1, line 8, "may" should read --many--.

In the Claims
Column 8, line 14, Claim 1, "member" should read --members--.

Signed and Sealed this
Twenty-fifth Day of August, 2015

Michelle K. Lee
*Director of the United States Patent and Trademark Office*